United States Patent [19]
Sreebny et al.

[11] Patent Number: 5,510,122
[45] Date of Patent: Apr. 23, 1996

[54] PREPARATION AND USE OF WHOLE SALIVA

[75] Inventors: Leo M. Sreebny, East Setauket; Steven S. Schwartz, Melville; Allen G. Meek, Poquott, all of N.Y.

[73] Assignee: The Research Foundation of State University of New York, Albany, N.Y.

[21] Appl. No.: 314,515

[22] Filed: Sep. 28, 1994

[51] Int. Cl.$^6$ ..................................... A61K 7/28
[52] U.S. Cl. ..................... 424/537; 514/902; 424/550
[58] Field of Search ................ 424/49, 50, 550, 424/537; 514/902

[56] References Cited

U.S. PATENT DOCUMENTS

| | | | |
|---|---|---|---|
| 2,684,924 | 7/1952 | Rose et al. | 167/30 |
| 4,438,100 | 5/1984 | Balslev et al. | 424/104 |
| 4,817,632 | 4/1989 | Schramm | 128/769 |
| 4,938,963 | 7/1990 | Parnell | 424/48 |
| 5,103,836 | 4/1992 | Goldstein et al. | 128/760 |
| 5,128,132 | 7/1992 | Parnell | 424/195.1 |

OTHER PUBLICATIONS

J. Toljanic, et al.–"Evaluation of the Substantivity of a Chlorhexidine Oral Rinse in Irradiated Head and Neck Cancer Patients", J. Oral. Maxillofac. Surg. 50: 1055–1059 (1992).
L. Sreebny–"Zerostomia, Xerosis, and Systemic Disease", The Female Patient 17: 14–28 (1992).
M. Seward, ed.–"Saliva, Its Role In Health and Disease" International Dental Journal 42: 291–304 (1992).
A. Veksler, et al.–"Reduction of Salivary Bacteria By Pre--Procedural Rinses with Chlorhexidine 0.12%", J. Periodontol. 62: 649–651 (1991).
M. Addy, et al.–"The Effect of Some Chlorhesidine–Containing Mouthrinses on Salivary Bacterial Counts", J. Clin. Periodontol. 18: 90–93 (1991).
Kalfas, S. and Rundegren, J.–"Biological Quantities of Salive Sterilized By Filtration Or Ethylene Oxide Treatment", Oral Microbiol. Immunol. 6: 182–186 (1991).
F. Spijkervet, et al.–"Chlorhexidine Inactivation By Saliva", Oral Surg. Oral Med. Oral Pathol. 69: 444–449 (1990).
L. Sreebny, et al.–"A Symposium On the Endogenous Benefits of Saliva In Oral Health", Compend. Cont. Educ. Dent. (Suppl.) 13: S450–S488 (1989).
L. Sreebny, et al.–"Xerostomia. Part I: Relationship to Other Oral Symptoms And Salivary Gland Hypofunction", Oral Surg. Oral Med. Oral Pathol. 66: 451–8 (1988).
L. Sreebny, et al.–"Xerostomia. Part II: Relationship to Nonoral Symptoms, Drugs and Diseases", Oral Surg. Oral Med. Oral Path. 68: 419–427 (1989).
L. Sreebny, et al.–"Xerostomia, A Neglected Symptom", Arch. Intern. Med. 147: 1333–1337 (1987).
L. Sreebny, et al.–"A Reference Guide to Drugs and Dry Mouth", Gerodontology 5: 75–99 (1986).
G. Silverman–"Sterilization By Ionizing Irradiation", pp. 89–97, in *Disinfection Sterilization and Preservation*, 3rd Ed., S. Block, Lea & Febiger 1983.
C. Williams, et al.–"Sterilization And Storage of Saliva", J. dent. Res. 42: 1416–1428 (1963).

*Primary Examiner*—Brian M. Burn
*Attorney, Agent, or Firm*—Hoffmann & Baron

[57] ABSTRACT

The preparation of a saliva composition substantially viable for therapeutic use in saliva-deficient individuals involves exogenously treating saliva to inactivate microorganisms by contacting with chlorhexidine or ionizing radiation. Pharmaceutically active agents may be added to the saliva composition.

19 Claims, No Drawings

PREPARATION AND USE OF WHOLE SALIVA

BACKGROUND OF THE INVENTION

1. Field of the Invention

The invention relates to the preparation of sterile, exogenous, whole saliva and a method of treating saliva deficient subjects by oral administration of this preparation.

2. Description of the Related Art

The principal protector of oral tissues is saliva produced by the salivary glands. Under some conditions, the functioning of the salivary glands becomes impaired or destroyed. Particularly devastating to the salivary glands are therapeutic irradiation used to treat head and neck cancer, and disease conditions such as AIDS, Grafts versus Host Disease (GHVD) and a wide variety of connective tissue and/or autoimmune disorders such as Sjogren's syndrome, rheumatoid arthritis, systemic lupus erythematosus and scleroderma. When the function of the salivary glands is reduced by 50% or more, individuals complain of dry mouth (xerostomia).

When the salivary glands are impaired or destroyed, serious complications follow. Included among these complications are inflammation, infection, ulceration and pain of the oral tissues. Also present are severe oral dryness, dysgeusia, dysphonia and dysphagiao These changes affect morbidity, profoundly alter the patient's quality of life, contribute to a loss of weight and often lead to significant compliance problems.

Attempts made to solve the problems related to impaired salivary glands have met with only limited success. Efforts to stimulate a patient's residual saliva producing capability depends on the presence of viable salivary gland tissue which may be non-existent or barely present.

A number of saliva substitutes are available for the treatment of xerostomia (dry mouth). Such substitutes are described, for example in U.S. Pat. Nos. 5,128,132, 4,938, 963 and 4,438,100. These substitutes however, do not contain the wide array of naturally occurring proteins which are responsible for the natural protective properties of saliva.

Saliva, unlike other body fluids such as blood, contains a very high concentration of microorganisms which are indigenous or acquired oropharyngeal flora. These microorganisms should be inactivated if saliva is to be stored for any period of time. Many types of sterilization, however, damage the salivary proteins.

Whole saliva has been treated by filtration, ethylene oxide, hydrogen peroxide and gamma or ultraviolet radiation for use as a laboratory culture medium by C. J. Williams, et al., "Sterilization and Storage of Saliva" *J. dent. Res* 42:1416–1428 (1963), who determined that 3% ethylene oxide was effective only at 37° C. This temperature alone can be damaging to the proteins. UV radiation was effective only with prefiltered saliva. However, filtration removes important proteins. The other methods excessively denatured the proteins.

More recently, saliva has been treated with dithiothreitol (DTT) and similarly sterilized by filtration or ethylene oxide treatment for use as a laboratory culture medium for oral bacteria by Kalfas and Rundegren, "Biological Quantities of Saliva Sterilized By Filtration or Ethylene Oxide Treatment", *Oral Microbiol. Immunol.* 6:182–186 (1991). These methods were found to cause denaturation and depolymerization of salivary proteins or to filter out protein. Moreover, the DTT is toxic to humans.

Chlorhexidine has been used as an oral rinse, see e.g., M. Addy et al., "The Effect of Some Chlorhexidine Containing Mouthrinses on Salivary Bacterial Counts," *J. Clin. Peridontal.* 18:90–93 (1991). There has been no suggestion to collect saliva and treat it with chlorhexidine.

Accordingly, it is an object of the invention to provide a method for sterilizing or disinfecting collected saliva while preserving its protective properties, particularly its proteins.

It is a further object of the invention to provide a method of treating persons with impaired salivary glands by administering sterilized or disinfected autologous saliva which substantially retains protective proteins.

SUMMARY OF THE INVENTION

The invention is a method for treating collected intact saliva to inactivate microorganisms contained therein while substantially maintaining the integrity of the salivary proteins. To accomplish this, the saliva is contacted with a disinfecting/sterilizing agent for a sufficient period of time to inactivate the microorganisms. The disinfecting/sterilizing agent is chlorhexidine or an ionizing radiation.

The invention is also a method for treating a subject with decreased natural saliva flow by orally administering to the subject a composition comprising natural saliva which has been treated to inactivate microorganisms by contacting with chlorhexidine or ionizing radiation while substantially maintaining the integrity of the naturally occurring salivary proteins.

Advantageously, the method for treating saliva allows the treated material to be stored without degradation until needed. Meanwhile, the integrity of the protective proteins is substantially maintained.

A further advantage is that whole saliva, which is vastly superior to any saliva substitute, can be stored and used to treat saliva-deficient subjects.

DETAILED DESCRIPTION OF THE INVENTION

The naturally-occurring components of saliva allow it to carry out critical functions such as lubrication of the mouth and esophagus, aid in mastication, swallowing, stimulation of the taste buds, and maintenance of cleanliness of the oral tissues and teeth. No "ersatz" saliva substitutes contain the wide array of components, particularly proteins, which are responsible for saliva's protective properties.

Saliva is a clear, slightly acid or alkaline, secretion from the parotid, submaxillary, sublingual and minor salivary glands of the mouth. Mammalian saliva contains a high percentage of water (98–99.5%) and important components including mucins, glycoproteins, salts and proteins such as amylase, serum albumin, globulins, antibacterial substances such as lysozyme and a mildly hemostatic agent. Saliva also contains blood group factors.

It has now been found that saliva can be collected from patients before they begin a course of therapeutic radiation or medication which will affect the salivary glands. A patient's autologous saliva may be treated, stored and used to alleviate oral symptoms after the patient's salivary glands have been impaired. By autologous is meant derived from the same individual. It is also possible to collect saliva from donors for a saliva bank. The collected saliva can be treated, stored and, when needed, returned to patients with the protective components of the saliva intact.

Because of the billions of microorganisms saliva contains, collected saliva is subject to rapid degradation. It is therefore necessary to substantially disinfect or sterilize the collected saliva so that it may be stored. It was important to develop a technique which substantially disinfects, preserves or sterilizes saliva but does not alter its protective proteins. The methods previously used to sterilize saliva proved to be unacceptably damaging in this regard.

It has been discovered that radiation and/or certain antimicrobial agents can be used to sterilize or substantially disinfect saliva with minimal or no damage to the protective properties. The preferred radiation is beta and the preferred antimicrobial agent is chlorhexidine.

The antimicrobial agent chlorhexidine has the chemical name N,N''-bis(4-chorophenyl)-3,12-diimino2,4,11,13-tetraazatetradecaneiimidamide with the chemical formula

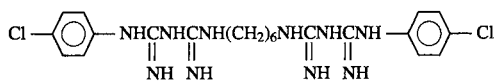

Chlorhexidine is commercially available as the diacetate salt $C_{22}H_{30}Cl_2N_{10} \cdot 2C_2H_4O_2$; as the digluconate salt $C_{22}H_{30}CL_2N_{10} \cdot 2C_6H_{12}O_7$; or as the dihydrochloride salt $C_{22}H_{30}Cl_2N_{10} \cdot 2HCl$; and is described in U.S. Pat. No. 2,684,924. The diacetate salt is soluble in alcohol, glycols and glycerols. The digluconate and dihydrochloride are soluble in water.

The chlorhexidine preferred herein is water soluble and added to collected saliva to attain a chlorhexidine concentration of at least 0.03 percent by weight. The range of concentration of chlorhexidine is preferably from about 0.01% to about 50% with a most preferred range of about 0.03% to about 0.12%.

Chlorhexidine, at a concentration as low as 0.03%, renders saliva sterile and exerts virtually no effect on the types and concentrations of proteins or the viscosity. For example, the amylase activity is only modestly reduced when a treated saliva is kept at room temperature for a week. To reduce loss of amylase activity, the chlorhexidine-treated saliva is preferably refrigerated, e.g., at 8° C. or normal refrigerator temperatures to −70° C. Ordinary freezers generally have a temperature of −18° C., and special freezers, −70° C.

The method used herein for chemical treatment of collected saliva involves collecting and optionally freezing, lyophilizing and reconstituting the collected saliva. This technique allows storage of the saliva as a dry power in microbial stasis. The powder is activated by the addition of water plus chlorhexidine. Alternatively, one can add chlorhexidine while collecting saliva; then lyophilize and store. Other additives can be added with the chlorhexidine or before the saliva is administered.

Radiation sterilization of medical supplies has employed ionizing radiation, usually in the form of cobalt-60 gammas (See, McGraw-Hill Encyclopedia of Science & Technology, Vol. 15 p.120, McGraw-Hill, Inc., New York 1987).

In this invention, the preferred radiation is beta or electron radiation. Beta radiation is obtained with a linear accelerator which is a device for accelerating electrons or positive ions through loaded waveguides by high frequency pulses or oscillations of the correct phase. A beta detector measures beta radiation. Methods for obtaining beta radiation are known in the art.

Saliva which is exposed to 2.5 kGy of electron-beam radiation or treated with chlorhexidine is rendered sterile. Total protein, as well as the number and intensity of individual proteins are minimally affected and there is no change in the viscosity of the saliva. Amylase activity declines somewhat by a maximum of about 25%.

In healthy persons, saliva is constantly secreted and swallowed throughout the day. The normal resting flow of whole saliva is about 0.3–0.4 mL/min.; the stimulated flow, about 1–2 mL/min. During the day the total secretion in an individual is about 400 to 600 mL.

Radiotherapy for head and neck cancer patients has a duration of about 40 days. In such a long course of therapy, if total saliva replacement were undertaken, a great volume of replacement material would be needed. However, it has been found that the replacement need not be total and only a fraction of the amount of natural flow is needed. This is because in persons in whom the salivary glands are damaged, salivary flow and swallowing (the sine-qua-non of oral clearance) may be virtually absent. Thus, substances which are placed in the mouth, e.g., via a spray, tend to remain there. Indeed, it has been recently shown that a commercially prepared 0.12% solution of chlorhexidine rinse alone is retained in the mouth for up to four hours in irradiated patients. Toljanic et al., "Evaluation of the Substantivity of a Chlorhexidine Oral Rinse In Irradiated Head and Neck Cancer Patients" *J. Oral Maxillofac Surg.* 50: 1055–1059 (1992). A chlorhexidine rinse alone, however contains no protective proteins or other components of saliva.

The volume of the residual saliva, i.e., the saliva present in the mouth after swallowing, varies between 0.2 and 0.8 mL in normal individuals. When one sprays the mouth with about 0.3 mL of saliva every hour for about 12 hours per day, one needs about 150 mL for a 40 day course of radiation therapy. This amount of saliva can readily be obtained from a patient prior to the onset of radiotherapy. Assuming a stimulated flow rate of about 1.5 mL/min, it will require only about five 10-minute periods of wax-chewing per day over a period of two days. In the same manner, even more saliva can be collected if desired.

We have observed that the flow and composition of saliva is normal in most head and neck cancer patients prior to their exposure to radiotherapy. It is possible to collect autologous saliva from these persons before they commerce their course of radiation, treat it to inactivate microorganisms, store it in a saliva-bank, and return it to the patient during the course of radiation. The collected and sterilized material can be offered to the patient in a spray bottle which delivers about 0.01 to 5 mL, preferably about 0.1 to 0.3 mL of solution per actuation.

The invention encompasses a method of treating oral mucosal dryness by administering a composition comprising disinfected and/or sterilized saliva to an affected patient.

Other components may also be added to the whole saliva. Pharmacologically active agents can also be added in conventional amounts and by conventional methods to produce salivary compositions as medicinal agents for administration to patients, e.g., mammals including humans. Pharmacologically active agents which can be added preferably include sialogogues such as parasympathiomimetic drugs e.g., pilocarpine up to about 15–20 mg/day, bromhexine, anthole trithione (e.g., Sialor® or Sulfarem®), bethanecol chloride (e.g., Duvoid®), up to 10–50 mg, 3–4 times/day; neostigmine bromide (e.g., Prostigmin®), up to 15 mg to 375 mg/day; organic acids such as citric acid (e.g., Bicitra®), up to 150 mL or more/day (0.32 molar solution) or 3–4 drops every 4 hours; ascorbic acid (vitamin C), e.g., 300 mg/day or more; etc. Sialogogues stimulate saliva flow. Antibacterials, antifungals, and antivirals known in the art can be added in standard dosage, e.g. sulfonamides, chloramphenicol, nitrofurazone, polymyxin, penicillins, quinolones, tetracycline, acyclovir. Some non-limiting examples are Bactrim®, Choromycetin®, Furacin®, Amoxil®, Cipro®, Floxin® and Symmetrel®.

The naturally-occurring constituents of saliva may be augmented by the incorporation of additional amounts of these constituents. These constituents include the following proteins: Albumin, amylase, beta-glucuronidase, carbonic anhydrase, cystatins, esterases, gustin, histatins, IgA (sIgA), IgG, IgM, kallikrein, lactoferrin, lactoperoxidase, LDH, lysozyme, mucins, phosphatases, polypeptides, e.g., hormones and epidermal growth factor, proline rich proteins, ribonucleases, serum proteins, statherin. Salivary constituents include the following electrolytes and other micromolecules: ammonia, bicarbonate, calcium, creatinine, fluoride, glucose, iodine, magnesium, nitrogen, phosphorous, potassium, sialic acid, sodium sulfates, thiocyanate, and uric acid. For more detailed discussion of these compounds which are constituents of saliva, see, e.g., *The Merck Index* published by Merck & Co., Inc., Rahway N.J. and references cited therein.

Each of these naturally occurring salivary constituents provides an important function. For example, the mucins, proline-rich proteins and water aid lubrication. Lactoferrin, lactoperoxidase, lysozyme, sIgA, mucins, histatins, cystatins and proline-rich proteins are anti-microbial. Calcium, phosphorous, P1, statherin and anionic proline-rich proteins aid remineralization. Water aids cleansing. $HCO_3$, $PO_4$ and non-specific buffers aid buffering. Amylase, lipase, proteases, nucleases, mucins and water serve digestive functions. Mucins, electrolytes and water maintain mucosal integrity. Gustin aids taste.

Natural saliva contains 98–99.5% water, and these other naturally occurring constituents of saliva are generally present in a total amount of up to about 2%. When any of these constituents are added to the composition of the invention, they will generally be added in amounts not appreciably greater than their natural occurrences, say up to a combined weight percent of, e.g., 5%.

It will be appreciated that the actual preferred amounts of active compound in a specific case will vary according to the specific compound being utilized and the particular compositions formulated. Dosage for a given subject can be determined using conventional considerations, e.g., by customary comparison of the differential activities of the active compound and of a known agent e.g., by means of an appropriate conventional pharmacological protocol.

It will also be appreciated that when the saliva composition is used to treat subjects with decreased saliva flow, the composition may be administered in effective amounts as needed to alleviate the mouth dryness and other symptoms with only practical limitations on amounts. If pharmacologically active compounds are added to the saliva compositions, the amount of active compound must be considered in determining dosage. The saliva compositions can also be diluted with water.

Additional inactive compounds may be added to adjust viscosity, taste, appearance or other physical properties. Viscosity enhancing substances include, e.g., glycerin and cellulose compounds such as carboxymethylcellulose. Amounts for these compounds can be determined by routine experimentation to achieve the desired effect.

The active treated saliva of the invention can also be employed in admixture with conventional excipients suitable for oral application and which do not deleteriously react with the active material. Suitable pharmaceutically acceptable carriers include, but are not limited to, water, salt solutions, gum arabic, vegetable oils, perfume oils such as peppermint, fatty acid monoglycerides and diglycerides, pertaerythrito fatty acid esters, hydroxmethylcellulose, polyvinyl pyrrolidone, glycerin, etc.

The pharmaceutical preparations can be sterilized as described above and if desired mixed with auxiliary agents, e.g., diluents, lubricants, preservatives, stabilizers, wetting agents, emulsifiers, salts for influencing osmotic pressure, buffers, coloring, flavoring and/or aromatic substances and the like which do not deleteriously react with the active compounds. They can also be combined where desired with other active agents, e.g., vitamins.

For oral application, particularly suitable are liquids, drops and sprays. Non-fermentable sugars or sugar substitutes, e.g., 1. sugar alcohols: a) sorbitol, b) xylitol, c) maltitol; 2. saccharines 3. aspartame 4. sucaryl or the like can be added wherein a sweetened vehicle is desired.

It is also possible to freeze-dry the composition and use the lyophilizate obtained for storage and later reconstitution. Also suitable are sprayable aerosol preparations wherein the active ingredient, optionally in combination with an additional inert carrier material, is packaged in a squeeze bottle or in admixture with a pressurized volatile, normally gaseous propellant, e.g., a freon. Aerosol preparations provide the treated saliva and optional additives directly to the oral tissue which needs to be treated.

The invention will be illustrated by the following non-limiting examples.

These examples describe a number of techniques which an be used to prepare a disinfected or sterilized autologous saliva. Total protein and SDS-PAGE were used as an index of the many proteins present in saliva. Amylase was measured as an index of enzyme activity. Viscosity was measured to assess the physical properties of the treated salivas and, indirectly, their mucin content.

For the following examples a total of ten healthy human subjects were used. They ranged in age between 21 and 71 years; none took any medications.

Methods and Materials: Wax-stimulated whole saliva was employed throughout the study. The samples were collected after an overnight fast or after a two hour period during which nothing was placed in the mouth. The saliva was examined in the fresh state or stored at −70° C. until used.

Amylase activity was determined by a modification of the Biomedix Amylotube® (Amylase) Reaction (Princeton Biomedix, Princeton-Highstown, N.J.). The determination of amylase is based on two-step procedure. These follow:

Step 1: Starch + $H_2O$ →(amylase)→colorless starch fragments

Step 2: Unhydrolyzed Starch + $I_2$ →colored starch-iodine complex

The color produced by the starch-iodine complex after 7.5 minutes of incubation of the starch substrate with the test sample, followed by the addition of the iodine reagent and 5 min. of color development, is compared to a reagent blank. The amylase present in the sample hydrolyzes the starch fragments which do not react with the iodine reagent. The decrease in absorbance (O.D.) at 660 nm is proportional to amylase activity in the sample.

(1) Preparation of the starch substrate: Add 1 part of the starch solution (Biomedix or Sigma) to 2 parts $H_2O$. The concentration of the starch solution =0.25 mg/mL.

(2) Incubate 0.5 mL of the above starch solution for 5 min. at 37° C.

(3) Prepare the salivary sample(s) at 1:400 dilution. Pipette 10 μL of the diluted saliva into the heated starch solution; a blank tube receives 10 μL of water in place of the saliva.

(4) Incubate the saliva/blank:starch samples for exactly 7.5 minutes at 37° C.

(5) Add 4 mL of water and 0.5 of the iodine solution (Biomedix or Sigma) to the above tubes.

(6) Read the tubes after 5 or 25 minutes at 660 nm. The results are expressed as amylotube units:

Amylotube units/dL=(O.D. reagent blank-O.D. saliva sample)/O.D. Reagent Blank ×1000×400

Total protein was determined according to the method of Pierce BCA® Protein Assay (Pierce, Rockford, Ill.)

The Pierce BCA® protein assay is a sensitive technique for the spectrophotometric determination of protein concentration. It is based on the reaction of proteins with $Cu^{2+}$ in an alkaline environment, yielding $Cu^{1+}$, with a sensitive reagent for $Cu^{1+}$, bicinchoninic acid (BCA). The standard employed in the tests is bovine serum albumin (BSA). The BSA is calibrated at final concentrations which vary from 0 to 100ug/mL. The test solutions are resting or stimulated whole saliva. The salivary samples are diluted at concentrations of 1:20, 1:40, 1:80 and, if necessary, 1:160 and higher. Pierce's "working reagent" is then prepared by mixing 50 parts of Pierce Reagent A to 1 part of Reagent B. Two hundred μg of the working reagent are added to 200 μg of the standard and test samples of saliva. These tubes are then incubated at 37° C. for one hour. The absorbance is read at 562 nm.

Viscosity was measured with a Brookfield Digital Viscometer.

Sterility was determined by inoculating samples of saliva into tubes which contained 4 mL of Brain Heart Infusion broth (Difco), followed by incubation aerobically at 37° C. and examination for growth after 24, 48 and 72 hours.

SDS-PAGE electrophoresis was conducted according to the method of Johnson, D. A. and Alvares, O. F., "Zinc Induced Changes in the Rat Parotid Salivary Proteins", J. Nutr. 114:1955 (1984).

The radiation studies were performed on a Linear accelerator (RDI Dynamatron OPC 1000) at Medical Sterilization, Inc. (Syosset, N.Y.).

The accelerator employed at Medical Sterilization Inc. (MSI) is a 4.5 MeV DYNAMITRON manufactured by Radiation Dynamics Inc. (RDI). It is a DC machine that operates at a beam current of 30 mA. The 1' diameter beam is accelerated vertically downward. After acceleration, the beam is magnetically scanned in a linear motion to produce a time average fluence that is uniform over a width of >48". The beam exits the vacuum into air through a thin titanium window, then traverses about 30" of air to the level of the four wheel automated cart system that conveys products to be irradiated. The width of the beam at the level of the cart is about 6" full width at half maximum (FWHM). Since the moving carts integrate through the gaussian shaped beam, the result of the irradiation is a dose that is uniform to within 5% over the surface of the cart. This film dosimetry traceable to National Institute for Standards and Technology (NIST) is used to measure the absorbed dose. At the rate the carts are moving, the full dose is delivered in a time interval of 4 to 8 seconds.

A Gray (Gy) is the SI unit of absorbed dose of energy from the decay of a radionucleotide. 1 Gy =1 Joule/kg.

EXAMPLE 1

Five individual samples of saliva from five adults were heated at 61° C. (pasteurization temperature) for 0, 5, 10, 15, 20 and 30 minutes. Determinations were made of total protein concentration, amylase activity, viscosity, sterility and electrophoretic patterns.

There appeared to be a modest decline in protein concentration with time, but these changes were not significant. In samples heated for 5 minutes, this amounted to about 2%. This slowly rose to 7% in samples heated for 30 minutes. Amylase activity progressively declined. The decline amounted to about 25% in samples heated for 5 minutes; 60% after 10 minutes; and 74% 86% and 90% respectively after 15, 20, and 30 minutes heating time. There was also a progressive decline in viscosity with time of heating. After 5 minutes the viscosity declined 30%; by 30 minutes, the decline was about 50%.

Inoculation of the samples of saliva into BHI broth revealed that some, but not all of the samples were rendered sterile after heating at 61° C. for 30 minutes.

Electrophoretic patterns of the samples heated at 61° C for 5 to 30 minutes were not different than a non-heated control.

EXAMPLE 2

Six individual samples of saliva from four adults were heated for 5 minutes at 25°, 55°, 61°, 65° and 100° C. Determinations were made of total protein concentration, amylase activity, viscosity, sterility and electrophoretic patterns.

The results showed that the total protein slightly decreased with increasing temperature, but the decline was not significant. The mean amylase activity declined 8% at 55° C., 17% at 61° C. and declined precipitously thereafter with a 61% loss at 65° C. and virtually no activity at 100° C. The viscosity for samples heated at 61° C. and 100° C. decreased 30% and 34% respectively.

The samples heated at 25° C. and 55° C. for 5 minutes and inoculated into BHI broth were all positive after 24 hours. The results of the samples heated at 61° C. were varied, some positive and some negative. Those heated at ≧65° C. showed no growth.

Electrophoretic patterns of the samples heated for 5 minutes at 24°, 55° and 61° C. were not different than a non-heated control. But at 65° C. and especially at 100° C., there was a marked diminution in the number and intensity of the bands.

EXAMPLE 3

Ten individual samples of saliva from five adults were collected, placed on ice and divided into the following groups:

1. (C): The control group; whole saliva

2. Ice/Sup: the supernatant of whole saliva which had been left standing, on ice, for 20 minutes.

3. Ice/Sup/Filt: the ice/sup further passed through a 0.45 micron Acrodisk filter.

4. Cent/Sup: the supernatant of whole saliva which was centrifuged, in the cold (8° C.) at 5000 rpm for 20 minutes.

5. Cent/Sup/Filt: the supernatant of the Cent/Sup further passed through a 0.45 micron Acrodisk filter.

Determinations were made of total protein concentration, amylase activity, viscosity, sterility and electrophoretic patterns.

As compared with the control, the Ice/Sup samples had a 26% loss of protein concentration. The Ice/Sup/Filt, Cent/Sup and Cent/Sup/Filt showed losses in total protein concentration of 47%, 43% and 51% respectively.

With regard to amylase activity, virtually no differences were observed between the control (whole saliva) the supernatants of saliva which stood on ice (Ice/Sup) or were centrifuged (Cent/Sup). The filtered salivas (Ice/Sup/Filt and Cent/Sup/Filt had about 12% loss of activity.

The viscosity results showed that keeping whole saliva on ice for 20 minutes (Ice/Sup) does not appreciably affect the viscosity of the supernatant fluid. The viscosity of centrifuged supernatant (Cent/Sup) was moderately reduced. Filtering the saliva through a 0.45 millipore filter (Ice/Sup/Filt and Cent/Sup/Filt reduces its viscosity to that of water.

The filtered samples (Ice/Sup/Filt and Cent/Sup/Filt) did not grow in BHI broth. The control and all other samples were positive.

Electrophoretic patterns of the controls, Ice/Sup and Cent/Sup showed no differences. The filtered samples (Ice/Cent/Sup/Filt and Cent/Sup/Filt) showed major losses in proteins, i.e., the number and intensity of the bands. This was particularly noticeable in the high molecular weight region.

EXAMPLE 4

Three individual samples of saliva from three adults were frozen at −70° C., transported to an irradiation facility (Medical Sterilization, Inc. Syosset, N.Y.) and subjected to doses of radiation which varied from zero to 2.5, 5, 10 and 20 kGy. Non-irradiated samples were used as controls. Determinations were made of total protein concentration, amylase activity, viscosity, sterility and electrophoretic patterns.

The results showed that exposure of the samples to radiation varying from 2.5 to 20 kGy did not significantly alter the total protein concentration. There was a progressive loss of amylase activity with increasing amounts of radiation. Exposure of the samples to 2.5 kGy resulted in a 26% loss of amylase activity, at 5 kGy the loss was about 43%. At higher doses, the decline in activity varied from 73% to 95%. The results also showed that the radiation had no effect on the viscosity.

All the irradiated salivary samples exhibited no growth when inoculated into BHI broth and incubated for up to 72 hours. The non-irradiated control samples were all positive.

Electrophoretic patterns of the control samples and those irradiated with 2.5 kGy were virtually the same. Increasing amounts of radiation produced a progressive loss in the number and intensity of protein bands as well as an enhancement of background staining.

EXAMPLE 5

Individual samples of saliva from six subjects were collected and aliquots were pooled. The individual, as well as the pooled samples were then frozen, lyophilized and stored at −70° C. The dried samples were subsequently reconstituted with deionized water to which was added chlorhexidine gluconate at final concentration of 0% (control), 0.03% by weight, 0.06%, and 0.12%.

Samples of the reconstituted salivas were incubated at 37° C. for 1, 3.5 and 7 days and left at room temperature, refrigerator temperature (8° C.), or freezer temperature (−18° C.) for 3.5 and 7 days.

Determinations were then made of total protein concentration, amylase activity, viscosity, sterility and electrophoretic patterns.

The results showed that addition of chlorhexidine to samples of lyophilized, reconstituted saliva did not alter the protein concentration. Moreover, no changes were observed in the samples which were incubated at 37° C., left at room temperature or maintained at 8° C. or for up to seven days.

The mean amylase activity for the 0 times control (without chlorhexidine) samples was not statistically different than the 0 time samples to which various concentrations of chlorhexidine had been added. When the samples containing 0.03%, 0.06% and 0.12% chlorhexidine were kept at 37° or room temperature for 3.5 to 7 days the amylase activity declined about 14 to 33%. The decline at 8° C. or −18° at 3.5 days was only slight and at 7 days was 3–18%. Therefore, activity decline can be avoided by keeping samples at lower temperatures.

Tests showed that lyophilization and subsequent reconstitution of saliva with water did not significantly alter the viscosity of the saliva.

Sterility tests for all samples were negative and showed no growth of microorganisms.

In regard to the electrophoretic patterns, except for the presence of a distinct blue staining chlorhexidine band situated at the bottom of the columns, no differences were observed between the SDS-PAGE gels which contained 0, 0.03%, 0.06% or 0.12% chlorhexidine. Nor were there any differences between the controls and those samples which were kept at 8° C. or −18° C. The gels of samples which were kept at 37° C. or room temperature for 3.5 to 7 days showed a progressive loss of a number of bands. The most prominent of these was the deeply stained blue band situated immediately below the amylase bands. The amylase bands, as well as many of the bands of the basic proline rich proteins were unchanged from the control sample.

Evaluation of the techniques: This study investigated a number of techniques that might be used to prepare an autologous saliva. Total protein and SDS-PAGE electrophoresis were used as an index of the proteins present in saliva. Amylase was measured as an index of enzyme activity. Viscosity was measured to assess the physical properties of the treated salivas and, indirectly, of the mucin content.

Each of the techniques had some advantages and disadvantages. A modified "Pasteurization" technique, where saliva was heated at 61° C. for 5, rather than the conventional 30 minutes, disinfected the saliva but, as anticipated, did not render it sterile. Only minor protein changes were observed, but there was about a 25–30% drop in amylase activity and viscosity. Severe losses were observed in samples which were heated at higher temperatures or for longer periods of time.

Radiation, was a simple and effective way to prepare an autologous saliva. High doses were required, as is the case with the sterilization of foods and medications. Saliva which was exposed to 2.5kGy of electron-beam radiation was rendered sterile. Although such doses can be obtained in any radiotherapy department, the time required, about 10 hours, would be prohibitive for large numbers of patients.

The total protein, as well as the number and intensity of individual proteins were barely affected by the radiation and there was no change in the viscosity of the saliva. Amylase activity declined by about 25%. A drawback to this technique is that it can only be practically performed in specialized laboratories. This makes it rather expensive. Moreover, some people oppose the use of substance or foods which have been irradiated.

Centrifugation and filtration induced profound losses (up to 50%) in the total protein concentration of the whole saliva. Moreover, the number and the intensity of the bands on SDS-PAGE electrophoresis were correspondingly reduced. Amylase activity showed little change. Not surprisingly, the filtered salivas were sterile and their viscosity was markedly reduced. Our protein findings do not agree with those of Kalfas and Rundegren.

The best and easiest way to prepare an autologous saliva was with the antibacterial agent, chlorhexidine. It rendered the saliva sterile at concentrations as low as 0.03%, and exerted virtually no effect, as observed by testing for total protein and examining SDS-PAGE gels, on the types and concentration of its proteins or on its viscosity. The amylase activity was modestly reduced when the treated salivas were incubated at 37° C. or at room temperature for about 1 week. This can be reduced or prevented by keeping the samples in the refrigerator until needed. The method which we used involved the freezing, lyophilization and reconstitution of the collected saliva. This technique allows us to present the autologous saliva as a dry powder which is activated by the addition of water with the chlorhexidine and, other agents as well e.g., pilocarpine. It can be offered to the patient in a spray bottle which delivers about 0.3 mL of the solution per actuation.

EXAMPLE 6

CLINICAL STUDY

A pilot study will be conducted on three selected patients who are to receive a course of head and neck radiation. The criteria for selection include: (1) that the patients are candidates for radiation therapy; (2) that no prior chemotherapy or surgery for this cancer was performed on these patients; and (3) that their stimulative salivary flow rate prior to the onset of radiation is within the normal range.

Tests are performed on the patients to determine the resting and stimulated flow rates of their saliva. Patients whose stimulated flow rates prior to radiation are between 1–2 mL/min. and who fulfill the selection criteria above are accepted into the study.

A minimum of 125 mL for a 40-day radiation period is collected prior to the radiation treatments. The patient is asked to chew gum (chicle, Nuttex) for 15 minutes, four times a day (with a 2 minute resting period between each masticatory cycle) over a period of two days. This provides about 180 mL of saliva.

The collected saliva is frozen at -70° C, lyophilized, divided into 6 equal portions, placed into 40 mL spray bottles (labeled Week 1 through Week 6) and stored in a refrigerator-freezer saliva bank at −18° C. Similarly labelled bottles, each of which contains an amount of dionized water calculated to reconstitute the original saliva volume (about 30 mL), and chlorhexidine at a final concentration of 0.12% will be stored in the refrigerator at about 8° C. During or following the course of radiation, each week, the patients add the water/chlorhexidine solution to the spray bottle which contains the lyophilized saliva, shake well, and spray 0.3 mL of this solution in their mouths every hour at least 10 hours per day. The spray bottles are designed to deliver 0.1 mL of saliva per actuation.

Samples of saliva will be collected from the patients every week during their 6-week course of radiation. The following tests will be performed on the saliva samples:

1. flow rates, resting and stimulated
2. pH
3. Buffer capacity
4. Viscosity
5. Total Protein
6. Amylase Activity
7. SDG-PAGE electrophoresis
8. Yeast (Candida) index
9. Lactobacillus index The patients are carefully monitored clinically. Semi-quantitative measurements will be made of the following symptoms:

1. xerostomia
2. dysphagia
3. dysphonia
4. dysgeusia
5. pain
6. mucositis/inflammation, ulceration.
   with a clinical rating of normal←0 1 2 3→severe code: 0=normal; 1=mild; 2=moderate; 3=severe When compared with patients who do not receive the autogous saliva, the treated patients are expected to experience alleviation of all of the above symptoms which normally result from the course of radiation treatment.

What is claimed is:

1. A method for treating saliva comprises collecting saliva; and contacting the saliva with a disinfecting agent to inactivate microorganisms contained in the saliva, said disinfecting agent comprising a chlorhexidine or up to 2.5 kGy ionizing radiation, said contacted saliva being substantially viable for therapeutic use.

2. The method of claim 1, wherein the chlorhexidine is water soluble.

3. The method of claim 1, wherein the concentration of chlorhexidine is from about 0.01% to about 50% by weight.

4. The method of claim 3, wherein the concentration of chlorhexidine is from about 0.03% to about 0.12% by weight.

5. The method of claim 1, wherein the ionizing radiation is beta radiation.

6. The method of claim 5, wherein the beta radiation is delivered by a linear accelerator.

7. The method of claim 5, wherein the radiation dosage is about 2.5 kGy.

8. The method of claim 1, further comprising lyophilizing the saliva for storage before or after the contacting.

9. The method of claim 1, wherein the therapeutic use is for the treatment of saliva-deficient individuals.

10. The method of claim 1, further comprising adding an effective amount of an additional pharmaceutically active agent to the saliva.

11. The method of claim 10, wherein the pharmaceutically active agent is a sialogogue.

12. The method of claim 11, wherein the sialogogue is selected from the group consisting of sympathiomimetic agents and organic acids.

13. A product of the method of claim 1.

14. The product of the method of claim 1, further comprising another pharmaceutically active agent.

15. A method for treating a saliva-deficient individual comprising orally administering to the individual an amount effective to alleviate xerostomia, of a composition comprising collected saliva which has been contacted with a disinfecting agent to inactivate microorganisms contained therein, said disinfecting agent comprising chlorhexidine or an ionizing radiation.

16. The method of claim 15, wherein the saliva is autologous.

17. The method of claim 15, wherein the composition is provided to the individual in aerosol form.

18. The method of claim 15, wherein the composition further comprises an effective amount of an additional pharmaceutically active agent having therapeutic effect for said individual.

19. The method of claim 18 wherein the pharmaceutically active agent is a sialogogue.

* * * * *